United States Patent
Pohl et al.

(10) Patent No.: US 7,541,487 B2
(45) Date of Patent: Jun. 2, 2009

(54) PROCESS FOR THE PREPARATION OF ISOCYANATES IN THE GAS PHASE

(75) Inventors: Fritz Pohl, Brunsbuttel (DE); Klaus Biskup, Leverkusen (DE); Rainer Bruns, Leverkusen (DE); Friedhelm Steffens, Leverkusen (DE); Herbert Stutz, Dormagen (DE)

(73) Assignee: Bayer MaterialScience AG, Leverkusen (DE)

( * ) Notice: Subject to any disclaimer, the term of this patent is extended or adjusted under 35 U.S.C. 154(b) by 0 days.

(21) Appl. No.: 12/001,235

(22) Filed: Dec. 11, 2007

(65) Prior Publication Data

US 2008/0146834 A1    Jun. 19, 2008

(30) Foreign Application Priority Data

Dec. 13, 2006    (DE) ...................... 10 2006 058 633

(51) Int. Cl.
*C07C 263/10*    (2006.01)
(52) U.S. Cl. ..................................... 560/347
(58) Field of Classification Search ................... 560/347
See application file for complete search history.

(56) References Cited

U.S. PATENT DOCUMENTS

| | | | |
|---|---|---|---|
| 4,847,408 A | 7/1989 | Frosch et al. | 560/347 |
| 5,391,683 A | 2/1995 | Joulak et al. | 528/67 |
| 5,449,818 A | 9/1995 | Biskup et al. | 560/347 |
| 5,633,396 A | 5/1997 | Bischof et al. | 560/347 |
| 5,679,839 A | 10/1997 | Armand et al. | 560/347 |
| 6,225,497 B1 | 5/2001 | Becker et al. | 560/347 |
| 7,084,297 B2 | 8/2006 | Woelfert et al. | 560/347 |
| 2005/0070734 A1 | 3/2005 | Wölfert et al. | 560/347 |
| 2006/0025556 A1* | 2/2006 | Koch et al. | 528/44 |

FOREIGN PATENT DOCUMENTS

WO    2007/014936 A2    2/2007
WO    2007/028715 A1    3/2007

* cited by examiner

*Primary Examiner*—Sikarl A Witherspoon
(74) *Attorney, Agent, or Firm*—Lyndanne M. Whalen

(57) ABSTRACT

An isocyanate is produced by reacting a primary amine with phosgene in the gas phase above the boiling point of the amine over an average contact time of 0.05 to 15 seconds under adiabatic conditions.

11 Claims, No Drawings

PROCESS FOR THE PREPARATION OF ISOCYANATES IN THE GAS PHASE

BACKGROUND OF THE INVENTION

The present invention relates to a process for the preparation of an isocyanate by reacting a primary amine with phosgene above the boiling point of the amine over an average contact time of from 0.05 to 15 seconds under adiabatic conditions.

Various processes for the preparation of isocyanates by reacting amines with phosgene in the gas phase are known from the state of the art. EP-A-593 334 describes a process for the preparation of aromatic diisocyanates in the gas phase in which the reaction of the di amine with phosgene takes place in a tubular reactor without moving parts and with a narrowing of the walls along the longitudinal axis of the reactor. The process is problematic, however, because the mixing of the educt streams only via a narrowing of the tube wall does not function well in comparison with the use of a proper mixing element. Poor mixing usually results in an undesirably high level of solids formation.

EP-A-699 657 describes a process for the preparation of aromatic diisocyanates in the gas phase in which the reaction of the appropriate diamine with phosgene takes place in a two-zone reactor. The first zone, which makes up about 20% to 80% of the total reactor volume, has an ideal mixing system and the second zone, which makes up 80% to 20% of the total reactor volume, has piston flow. However, because at least 20% of the reaction volume is ideally back-mixed, the resulting residence time distribution is non-uniform, which can lead to an undesirably increased level of solids formation.

EP-A-289 840 describes the preparation of diisocyanates by phosgenation in the gas phase. In this disclosed process, the reaction takes place in a turbulent flow at temperatures between 200° C. and 600° C. in a cylindrical chamber without moving parts. The omission of moving parts reduces the risk of a phosgene leak.

Disregarding fluid elements in the vicinity of the wall, the turbulent flow in the cylindrical chamber (tube) achieves a relatively good equidistribution of the flow in the tube and hence a relatively narrow residence time distribution, which, as described in EP-A-570 799, can lead to a reduction in solids formation.

EP-A-570 799 discloses a process for the preparation of aromatic diisocyanates in which the reaction of the appropriate diamine with phosgene is carried out in a tubular reactor above the boiling point of the diamine over an average contact time of from 0.5 to 5 seconds. As described in the specification, both excessively long and excessively short reaction times lead to unwanted solids formation, so a process is disclosed in which the average deviation from the average contact time is less than 6%. Observation of this contact time is achieved by carrying out the reaction in a tubular flow characterized either by a Reynolds number of over 4000 or by a Bodenstein number of over 100.

EP-A-749 958 describes a process for the preparation of triisocyanates by the gas phase phosgenation of (cyclo)aliphatic triamines having three primary amine groups in which the triamine and the phosgene are reacted together continuously in a cylindrical reaction chamber heated to 200° to 600° C., with a flow velocity of at least 3 m/s.

EP-A-928 785 describes the use of microstructure mixers for the phosgenation of amines in the gas phase. A disadvantage of using such micromixers is that even the smallest amounts of solids, whose formation cannot be completely ruled out in isocyanate synthesis, can lead to clogging of the mixer, thereby reducing the time for which the phosgenation plant is available.

WO 03/045900 describes in detail the preparation of isocyanates on an industrial scale by means of gas phase phosgenation. As explained in WO 03/045900, there are two possible technical methods for carrying out the known gas phase phosgenation processes, which use a cylindrical reaction chamber. In the first method, the reaction can be carried out in a single length of tube whose diameter has to be commensurate with the production capacity of the plant. According to WO 03/045900, this design has the disadvantage, for very large production plants, that it is no longer possible to accurately control the temperature of the reaction streams in the core of the flow by heating the wall of the tube. Local temperature inhomogeneities can lead to (a) decomposition of the product if the temperature is too high or (b) inadequate conversion of the educts to the desired isocyanate if the temperature is too low.

The second possible technical method, namely division of the reaction mixture into individual partial streams that are then passed in parallel through smaller individual tubes whose temperature can be controlled better on the basis of their smaller diameter, is also regarded by WO 03/045900 as disadvantageous. According to WO 03/045900, a disadvantage of this process variant is that it is susceptible to clogging if the volumetric flow rate is not regulated through each individual tube. WO 03/045900 substantiates this by explaining that when a sediment deposits at some point in one of the tubes, the pressure loss of the flow through this tube increases and the reaction gas then automatically switches increasingly to other tubes. The consequence of this is that less gas flows through the tube containing the sediments, so the flow through the tube experiences an increased residence time, which, as already explained in EP-A-570 799, leads to an increase in solids formation.

In summary, WO 03/045900 explains that, in industrial gas phase phosgenations, the use of one large tube has the problem of temperature control of the whole flow, and the use of many small tubes runs the risk of non-uniform flow through the tubes.

According to the teaching of WO 03/045900, the disadvantages outlined can be avoided and the continuous phosgenation of amines in the gas phase can be carried out advantageously, with a substantial increase in the number of operating hours of the production plant, if the reaction is carried out in a non-cylindrical reaction channel, preferably a plate reactor, whose height preferably affords an advantageous temperature control of the reactants, and whose width is at least twice the height. As WO 03/045900 further explains, the height of the reaction channel is not generally restricted and the reaction can be carried out in a reaction channel with a height of, e.g., 40 cm. However, if a better heat exchange with the reactor walls is to be obtained, WO 03/045900 teaches that the reaction should be carried out in reaction channels of small height, e.g., only a few centimeters or millimeters, and hence with reactor dimensions at which— as WO 03/045900 indicates when commenting on EP-928 758—even the smallest amounts of solids, whose formation cannot be completely avoided in isocyanate synthesis, can lead to clogging of the reactor, thereby reducing the time for which the phosgenation plants are available.

SUMMARY OF THE INVENTION

Surprisingly, it has now been found that the preparation of isocyanates by reacting appropriate primary amines with phosgene in the gas phase can be carried out under adiabatic conditions by ensuring that the average residence time in the reaction chamber is 0.05 to 15 s. It is thus possible, advantageously and independently of the reactor geometry, to avoid temperature control problems and to obtain isocyanates on an industrial scale with high space/time yields and a substantially increased number of operating hours of the production plant.

DETAILED DESCRIPTION OF THE INVENTION

The present invention provides a process for the preparation of isocyanates by reacting appropriate primary amines with phosgene in which phosgene and the primary amine(s) are reacted above the boiling point of the amine(s) over an average contact time of 0.05 to 15 seconds, the reaction being carried out under adiabatic conditions.

Preferably, the process of the present invention comprises one or more of the following steps a)-d), it being particularly preferred to carry out all the steps a)-d). The steps a)-d) are as follows:

a) the vaporized amine(s), optionally diluted with an inert gas or with the vapors of an inert solvent, and phosgene are heated separately to temperatures of from 200 to 600° C. and continuously mixed, b) the reaction mixture made up of vaporized amine and phosgene is passed continuously through a reaction chamber, while avoiding back-mixing, and reacted therein over an average contact time of 0.05 to 15 seconds under adiabatic conditions, c) the gas mixture leaving the reaction chamber is cooled to condense the isocyanate formed, the temperature being kept above the decomposition point of the carbamyl chloride(s) corresponding to the reacted amine(s), and d) uncondensed isocyanate is separated from the gaseous mixture by scrubbing with a liquid.

Preferably, the reaction chamber used in step b) has a rotationally symmetric geometry with a constant or increasing flow area in the direction of flow of the reaction mixture. Preferably, the reaction chamber used is a tubular reactor with a substantially constant or increasing flow area in the direction of flow of the reaction mixture. In another preferred embodiment, the reaction chamber, preferably a tubular reactor, has sections of constant and increasing flow area in the direction of flow.

The embodiment of the invention in which the reaction chamber has a rotationally symmetric geometry and a cascade-like and/or continuous change in the flow area in the direction of flow, has the advantage that the flow velocity along the axis of the reaction chamber can be adjusted. Because of the volume increase during phosgenation, a constant flow area in the direction of flow results in an acceleration of the flow. By suitably widening the flow area in the direction of flow, the flow velocity of the reaction mixture can be kept constant over the length of the reactor, thereby increasing the available reaction time for the same reactor length. This advantage is especially important when reacting relatively unreactive aromatic amines.

Primary amines can be used as starting materials in the process of the present invention. It is preferable to use primary amines which can be converted to the gas phase without decomposition. Particularly suitable amines, especially diamines, are those based on aliphatic or cycloaliphatic hydrocarbons having 1 to 15 carbon atoms. Examples of preferred amines are 1,6-diaminohexane, 1-amino-3,3,5-trimethyl-5-aminomethylcyclohexane (IPDA) and 4,4'-diaminodicyclo-hexylamine. Use of 1,6-diaminohexane (HDA) is particularly preferred.

Aromatic amines, preferably those which can be converted to the gas phase without decomposition, can also be used as starting materials for the process of the present invention. Examples of preferred aromatic amines are toluenediamine (TDA), especially 2,4-TDA and 2,6-TDA and mixtures thereof; diaminobenzene; naphthyldiamine (NDA); and 2,2'-, 2,4'- or 4,4'-methylenediphenyldiamine (MDA) or mixtures of these isomers. Toluenediamine (TDA) is particularly preferred, especially 2,4-TDA and 2,6-TDA and mixtures thereof. Before the process of the present invention is carried out, the starting amine is normally vaporized heated to 200° C. to 600° C., preferably 201° C. to 500° C., most preferably from 250° C. to 450° C., and optionally diluted with an inert gas, such as $N_2$, He or Ar, or with the vapors of an inert solvent, e.g., an optionally halogen-substituted aromatic hydrocarbon such as chlorobenzene or o-dichlorobenzene and introduced into the reaction chamber.

The vaporization of the starting amine(s) can take place in any known evaporating apparatus. Preferred evaporating systems are those in which a small operating hold-up is passed through a falling-film evaporator with a high circulation efficiency, where, in order to minimize the thermal stressing of the starting amine(s), the evaporation process is optionally supported—as explained above—by feeding in inert gas and/or vapors of an inert solvent. The vaporized amine(s) may still contain unvaporized droplets of amine(s) (aerosol). Preferably, however, the vaporized amine(s) contains essentially no droplets of unvaporized amine(s), (i.e., at most 0.5 wt. % of amine, more preferably no more than 0.05 wt. % of amine, based on the total weight of amine is present in the form of unvaporized droplets and the remainder of the amine is present in vapor form). It is most preferred that the vaporized amine(s) contain no droplets of unvaporized amine(s). Preferably, after vaporization, the vaporized amine, optionally diluted with inert gases or inert solvent vapors, is brought to the desired feed temperature by means of an after-heater.

In a preferred embodiment of the invention, the vaporization and superheating of the starting amine(s) takes place in several stages in order to avoid unvaporized droplets in the vaporized amine stream. It is particularly preferred to use multi-stage evaporation steps in which droplet separators are incorporated between the evaporating and superheating systems and/or the evaporating apparatuses also act as a droplet separator. Suitable droplet separators are described, e.g., in "Droplet Separation", A. Burkholz, VCH Verlagsgesellschaft, Weinheim—New York—Basle—Cambridge, 1989. Particularly preferred droplet separators are those which cause a low pressure loss. Most preferably, the vaporized amine is brought to the desired feed temperature by means of an after-heater that also acts as a droplet separator. This after-heater preferably has a liquid outlet for continuous emptying of the separator. The reactor running time is markedly increased by making the vaporized starting amine stream essentially droplet-free before it enters the reactor.

In the process of the present invention, it is advantageous to use an excess of phosgene relative to amino groups. The molar ratio of phosgene to amino groups is conventionally from 1.1:1 to 20:1, preferably 1.2:1 to 5:1. The phosgene is also heated to temperatures of from 200° C. to 600° C. and optionally diluted with an inert gas, such as $N_2$, He or Ar, or with the vapors of an inert solvent, e.g., an optionally halogen-substituted aromatic hydrocarbon such as chlorobenzene or o-dichlorobenzene, before it is introduced into the reaction chamber.

The process of the present invention is carried out in such a way that the separately heated reactants are introduced into at least one reaction chamber, mixed and reacted under adiabatic conditions by observing suitable reaction times. The isocyanate is then condensed by cooling the gas stream down to a temperature above the decomposition point of the corresponding carbamyl chloride, namely toluenediamine acid chloride in the case of TDA, for example.

The residence time required to react the amine groups with the phosgene to give the product isocyanate is between 0.05 and 15 seconds, depending on the type of amine used, the starting temperature, the adiabatic temperature increase in the reaction chamber, the molar ratio of starting amine to phosgene and the extent of any dilution of the reactants with inert gases.

If, for the particular system (starting temperature, adiabatic temperature increase, molar ratio of reactants, diluent gas, starting amine), a predetermined minimum residence time for the complete reaction is exceeded by less than 20%, preferably less than 10%, the formation of secondary reaction products, such as isocyanurates and carbodiimides, can be extensively avoided.

Within this contact time spectrum, which is very narrow for chemical reactions, the reactants must be mixed as homogeneously as possible and the subsequent reaction must take place. The subsequent reaction preferably takes place without back-mixing, which would have the effect of widening the contact period and hence increasing the formation of unwanted by-products and secondary products.

When the process is carried out in practice, there may be a deviation from the average contact time due to the time required to mix the reactants. If the reactants are not yet homogeneously mixed, the reactor still contains unmixed or partially mixed volumes of gas in which there is still no contact or still incomplete contact between the reactants. The reactants should therefore preferably be mixed over a time of 0.01 to 0.3 second up to a degree of segregation of at least $10^{-1}$. The degree of segregation is a measure of the incompleteness of mixing (cf., for example, Chem.-Ing.-Techn. 44 (1972), p. 1051 et seq.; Appl. Sci. Res. (The Hague) A3 (1953), p. 279).

Methods for obtaining short mixing times are known in principle. Examples of suitable mixing apparatus include mixing units or mixing zones with moving or static mixing elements or nozzles. Static mixers such as those described, e.g., in EP-A-1 362 847, EP-A-1 526 129 or EP-A-1 555 258 are preferred.

After the reaction components have been mixed, the reaction mixture flows through the reaction chamber. Neither the mixing zone nor the adjoined reaction chamber has heating surfaces, which can give rise to thermal stressing resulting in secondary reactions such as isocyanurate or carbodiimide formation, or cooling surfaces, which can give rise to condensation resulting in sediments. The components are reacted under adiabatic conditions, the adiabatic temperature increase in the reactor is adjusted solely via the temperatures, compositions and relative proportions of the educt streams, and via the residence time in the reactor.

The flow through the reaction chamber should preferably take place in the form of an approximately 90% plug flow, so that all the parts of the flow volume have approximately the same flow time, thereby minimizing any further widening of the contact time distribution between the reactants. The degree of realization of the ideal plug flow (with an average deviation from the average residence time of 0) is described in flow technology by the Bodenstein number Bo (Fitzer, Techn. Chemie, Springer 1989, pp 288-295). Preferably, the Bodenstein number in the process according to the invention should be at least 10, preferably greater than 100 and most preferably greater than 250.

In step c), after the phosgenation reaction has taken place in the reaction chamber, the gaseous mixture continuously leaving the reaction chamber, which preferably comprises at least one isocyanate, phosgene and hydrogen chloride, is freed of the isocyanate formed. This can be achieved in a single stage by, e.g., selective condensation in an inert solvent, as already recommended for other gas phase phosgenations (EP-A-0 749 958).

Preferably, however, the condensation is achieved by spraying one or more appropriate liquid streams (quenching liquids) into the gaseous mixture leaving the reaction chamber. As described in EP-A-1 403 248, this affords a rapid cooling of the gaseous mixture without the use of cold surfaces. However, independently of the type of cooling, the temperature of the cooling zone is preferably chosen so that it is above the decomposition point of the carbamyl chloride corresponding to the isocyanate, and so that the isocyanate, and optionally the solvent concomitantly used in the amine vapor stream and/or phosgene stream as a diluent, condense or dissolve in the solvent, while excess phosgene, hydrogen chloride and any inert gas concomitantly used as diluent pass through the condensation or quenching stage. Solvents kept at a temperature of 80 to 200° C., preferably of 80 to 180° C., e.g. chlorobenzene and/or dichlorobenzene, or isocyanate kept in this temperature range, or mixtures of isocyanate with chlorobenzene and/or dichlorobenzene, are particularly suitable for selectively obtaining the isocyanate from the gaseous mixture leaving the reaction chamber.

Production of the flow, essential for the process according to the invention, of the gaseous reaction mixture extensively as a plug flow without substantial back-mixing through the reaction chamber from the mixing zone is assured by a pressure difference between the educt feed lines to the mixing zone and the outlet of the condensation or quenching stage. In general, the absolute pressure is 200 to 3000 mbar in the feed lines to the mixing zone and 150 to 2500 mbar downstream of the condensation or quenching stage. However, the maintenance of a pressure difference is essential only for the purpose of assuring the directed flow.

In step d), the gaseous mixture leaving the condensation or quenching stage is freed of residual isocyanate with a suitable scrubbing liquid in a downstream gas scrubber, and then freed of excess phosgene in known manner. This can be effected by means of a cold trap, by absorption in an inert solvent (e.g., chlorobenzene or dichlorobenzene) or by adsorption and hydrolysis on activated charcoal. The hydrogen chloride gas passing through the phosgene recovery stage can be recycled in known manner in order to recover the chlorine required for phosgene synthesis. The scrubbing liquid obtained in step d) after use in the gas scrubber is then preferably used in step c) as a quenching liquid for cooling the gaseous mixture leaving the tubular reactor.

The isocyanates are then preferably purified by distillative working-up of the solutions or mixtures from the condensation or quenching stage.

EXAMPLES

Example 1

"Non-Adiabatic Phosgenation of TDA"
(Comparative)

20 kg/h of a mixture made up of 2,4- and 2,6-toluenediamine in a weight ratio of 80% to 20% were vaporized and introduced into a tubular reactor in gaseous form at 400° C. Simultaneously, in a parallel operation, 100 kg/h of gaseous phosgene were heated to 310° C. and likewise introduced into the tubular reactor. The streams were injected into the mixing zone through a nozzle and mixed before entering the reaction chamber. The mixing zone was insulated to prevent heat losses before and during mixing. The reaction chamber was not thermally insulated and was cooled by thermal radiation. The reaction conditions were thus non-adiabatic. The gaseous mixture leaving the tubular reactor after 2.2 seconds had a final temperature of 380° C. and was cooled by injection of ortho-dichlorobenzene. The isocyanate formed was condensed, washed out and then worked-up by distillation by known methods. The pressure difference between the TDA feed line and the condensation stage was 200 mbar in order to achieve a directed flow of gas between the feed lines to the mixing zone and the condensation stage. After a reaction time of 96 h, the pressure in the TDA feed line increased sharply because the reaction chamber in the tubular reactor had been narrowed at the tube walls by sediments formed in the reaction. The formation of the sediments was attributable to increased by-product formation. The experiment therefore had to be terminated.

Example 2

"Adiabatic Phosgenation of TDA" According to the Invention 20.5 kmol/h of a mixture composed of 2,4- and 2,6-toluenediamine in a weight ratio of 80% to 20% were vaporized together with 500 kg/h of nitrogen and introduced in gaseous form into a tubular reactor at a temperature of 320° C. Simultaneously, in a parallel operation, 182 kmol/h of gaseous phosgene together with 1000 kg/h of ortho-dichlorobenzene were heated to 360° C. and likewise introduced into the tubular reactor. The streams were injected into the mixing zone through a nozzle and mixed before entering the reaction chamber. The mixing zone and the reaction chamber were thermally insulated so that neither additional heat input due to heating, nor heat dissipation due to external cooling or thermal radiation, took place. The reaction was thus carried out under adiabatic conditions. A final temperature of 405° C. was measured by means of surface thermometers at the outlet of the reaction chamber. The gaseous mixture leaving the reaction chamber after 5.5 seconds was cooled by the injection of ortho-dichlorobenzene and the isocyanate formed was condensed, washed out and then worked up by distillation by known methods. The pressure difference between the TDA feed line and the condensation stage was 60 mbar in order to achieve a directed flow of gas between the feed lines to the mixing zone and the condensation stage. No increase in the pressure difference was measured even after a reaction time of 720 h, indicating that no sediments were formed in the reaction. An inspection of the reaction chamber also gave no indication of residue formation.

Example 3

"Adiabatic Phosgenation of IPDA" According to the Invention 17.6 kmol/h of isophoronediamine were vaporized together with 42 kg/h of nitrogen, superheated to a temperature of 300° C. and introduced in gaseous form into a tubular reactor. Simultaneously, in a parallel operation, 64 kmol/h of gaseous phosgene were heated to 300° C. and likewise introduced into the tubular reactor. The streams were mixed over a mixing time of 0.02 sec and entered the reaction chamber. The mixing zone and the reaction chamber were thermally insulated so that neither additional heat input due to heating, nor heat dissipation due to external cooling or thermal radiation, took place. The reaction was thus carried out under adiabatic conditions. A final temperature of 450° C. was measured by means of surface thermometers at the outlet of the reaction chamber. The gaseous mixture leaving the reaction chamber after 0.1 s was cooled by the injection of monochlorobenzene and the isocyanate formed was condensed, washed out and then worked up by distillation by known methods. The pressure difference between the IPDA feed line and the condensation stage was 200 mbar and the pressure difference between the phosgene feed line and the condensation stage was 40 mbar in order to achieve a directed flow of gas between the feed lines to the mixing zone and the condensation stage. No pressure increase was observed even after a reaction time of 1000 h. No significant residue deposits were found in a subsequent inspection of the reaction chamber.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of an isocyanate comprising reacting in the gas phase a primary amine with phosgene at a temperature above the amine's boiling point over an average contact time of 0.05 to 15 seconds under adiabatic conditions.

2. The process of claim 1 further comprising: (i) condensing the isocyanate in the primary amine and phosgene reaction mixture by cooling the isocyanate-containing gas stream to a temperature above the corresponding carbamyl chloride's decomposition point, (ii) removing excess phosgene from the primary amine and phosgene reaction mixture, and (iii) recycling hydrogen chloride gas to recover chlorine for use in phosgene synthesis.

3. The process of claim 1 in which the amine is vaporized and optionally diluted with an inert gas or with vapors of an inert solvent and heated to a temperature of from 200 to 600° C. to form vaporized amine containing essentially no droplets of unvaporized amine, prior to reaction with the phosgene.

4. The process of claim 1 further comprising:
a) heating the amine gas, optionally diluted with an inert gas or with vapors of an inert solvent, and phosgene separately to temperatures of from 200 to 600° C. and continuously mixing the amine and phosgene to produce a gaseous reaction mixture,
b) continuously passing the gaseous mixture produced in step a) through a reaction chamber without back-mixing, and reacting the amine and phosgene therein over an average contact time of from 0.05 to 15 seconds under adiabatic conditions to form an isocyanate-containing gas stream,
c) cooling the isocyanate-containing gas stream leaving the reaction chamber to a temperature greater than decomposition point of the amine's corresponding carbamyl chloride to condense the isocyanate, and
d) separating uncondensed isocyanate from the gas stream by scrubbing with a liquid.

5. The process of claim 4 in which the reaction chamber has a rotationally symmetric geometry with a constant or increasing flow area in the reaction mixture's direction of flow.

6. The process of claim 4 in which the reaction chamber has sections of constant and increasing flow area in the direction of flow.

7. The process of claim 4 in which the gaseous mixture leaving the reaction chamber comprises at least one isocyanate, phosgene and hydrogen chloride, and the gaseous mixture is cooled in step c) by having at least one liquid stream sprayed into it.

8. The process of claim 7 in which at least part of the scrubbing liquid obtained in step d) after use in the gas scrubber is used in step c) for cooling the gaseous mixture leaving the reaction chamber.

9. The process of claim 7 in which at least part of the mixture obtained after condensation in step c) is used in step c) for cooling the gaseous mixture leaving the reaction chamber.

10. The process of claim 1 in which the isocyanate is toluene diisocyanate, methylenediphenyl diisocyanate, dicyclohexylmethane diisocyanate, hexamethylene diisocyanate and/or isophorone diisocyanate.

11. The process of claim 3 in which the vaporized amine does not contain any droplets of unvaporized amine.

* * * * *